United States Patent [19]

Wegman et al.

[11] Patent Number: 4,511,741

[45] Date of Patent: Apr. 16, 1985

[54] PRODUCTION OF ALDEHYDES FROM ORGANIC ACID ESTERS

[75] Inventors: Richard W. Wegman, South Charleston; David C. Busby, Cross Lanes, both of W. Va.

[73] Assignee: Union Carbide Corporation, Danbury, Conn.

[21] Appl. No.: 557,269

[22] Filed: Dec. 2, 1983

[51] Int. Cl.$^3$ .................. C07C 45/49; C07C 45/50
[52] U.S. Cl. .................. 568/484; 568/485; 568/489
[58] Field of Search .................. 568/484, 485, 489

[56] References Cited

U.S. PATENT DOCUMENTS

| | | | |
|---|---|---|---|
| 3,356,734 | 12/1967 | Kuraishi et al. | 568/489 |
| 3,720,718 | 3/1973 | Fenton | 568/484 |
| 3,784,616 | 1/1974 | Fenton | 568/484 |
| 4,189,441 | 2/1980 | Braca et al. | 560/232 |
| 4,225,517 | 9/1980 | Gane | 568/487 |
| 4,239,704 | 12/1980 | Pretzer et al. | 568/487 |
| 4,251,458 | 2/1981 | Pugach | 568/484 |
| 4,267,384 | 5/1981 | Smith | 568/462 |
| 4,429,150 | 1/1984 | Drent | 568/484 |
| 4,447,648 | 3/1984 | Wegman | 568/484 |

FOREIGN PATENT DOCUMENTS

| | | | |
|---|---|---|---|
| 0022735 | 1/1981 | European Pat. Off. | 568/487 |
| 0025702 | 3/1981 | European Pat. Off. | 560/232 |
| 0026280 | 4/1981 | European Pat. Off. | 568/487 |
| 0028474 | 5/1981 | European Pat. Off. | 568/484 |
| 0028515 | 5/1981 | European Pat. Off. | 568/484 |
| 0031606 | 7/1981 | European Pat. Off. | 568/484 |
| 0031784 | 7/1981 | European Pat. Off. | 560/232 |
| 2941232 | 4/1981 | Fed. Rep. of Germany | 560/232 |
| 4003 | 2/1973 | Japan | 568/484 |
| 52-136110 | 11/1977 | Japan | 568/487 |
| 52-136111 | 11/1977 | Japan | 568/487 |
| 52-133914 | 11/1977 | Japan | 568/487 |
| 2001070A | 1/1979 | United Kingdom | 560/232 |
| 2038829A | 7/1980 | United Kingdom | 568/489 |
| 2067557A | 7/1981 | United Kingdom | 568/484 |
| 2067556A | 7/1981 | United Kingdom | 568/484 |

OTHER PUBLICATIONS

J. Am. Chem. Soc., 1978, 100, 6238.
Fundamental Research of Homogeneous Catalysis, vol. 3, Plenum 1979, Braca et al.

*Primary Examiner*—Werren B. Lone
*Attorney, Agent, or Firm*—F. M. Fazio

[57] ABSTRACT

A process for the production of an aldehyde at high selectivity and rate by the reaction of an organic ester with carbon monoxide or synthesis gas in contact with a catalyst system containing rhodium atoms and cobalt atoms and lithium iodide or lithium bromide and, optionally, an organic ligand.

18 Claims, No Drawings

PRODUCTION OF ALDEHYDES FROM ORGANIC ACID ESTERS

BACKGROUND OF THE INVENTION

The production of organic compounds using carbon monoxide or synthesis gas, which is a mixture of carbon monoxide and hydrogen, as a reactant has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also known that esters, ethers, and other organic compounds can be reacted with carbon monoxide or synthesis gas to produce oxygenated organic compounds. The difficulties, however, have resided in the ability to carry out any one of these chosen reactions to produce the desired compound at acceptable efficiency, conversion rate and selectivity.

In almost all instances the reaction is generally catalyzed using a Group VIII transition metal compound as catalyst and halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of oxygenated organic compounds by the reaction of esters or alcohols with carbon monoxide or synthesis gas, to our knowledge it does not disclose or suggest our improved invention. Several of the pertinent patents in this area are discussed below.

In U.S. Pat. No. 3,356,734, issued to Kuraishi et al on Dec. 5, 1967, there is disclosed a process for producing acetaldehyde by the reaction of methanol with synthesis gas using a cobalt catalyst promoted by a halogen promoter. It contains no recognition of the benefits to be achieved with specific halogen promoters, nor does it suggest or disclose the use of mixtures of rhodium and cobalt or of initial reactants other than methanol.

The production of esters by the reaction of esters or ethers with synthesis gas is the subject of U.S. Pat. No. 4,189,441, issued to Braca et. al. on Feb. 19, 1980. The reaction is carried out using a ruthenium carbonyl and halogen promoter system. There is no specific mention of the metal atom combination of this invention or of lithium iodide and there is obtained a mixture of many products; the reaction is not selective and aldehydes were not observed. In related articles, J. Am. Chem. Soc., 1978, 100, 6238, and Fundamental Research of Homogeneous Catalysis, Vol. 3, Plenum (1979), Braca et al state that no acetaldehyde was found among the products.

On Sept. 30, 1980, U.S. Pat. No. 4,225,517 was issued to Gane. This patent claims a process for reacting methanol with synthesis gas for the production of acetaldehyde in the presence of a cobalt catalyst, an iodine or bromine promoter, a compound of one of the elements arsenic, antimony or bismuth and the additional presence of an additive which can be an inert liquid, or an acid or acid derivative, or an oxygen-containing compound, or a non-polar solvent. The selectivities reported are below 60%. The patent contains no recognition of the unexpected and unpredictable benefits to be achieved by the use of the mixture of rhodium and cobalt atoms or any single specific halogen compound. In column 10, lines 5 and 6, Gane indicates that the use of a trivalent phosphorus compound resulted in the production of ethanol as the major product rather than the production of acetaldehyde.

The Pretzer et. al. patent, U.S. Pat. No. 4,239,704, issued on Dec. 16, 1980, discloses a process for producing acetaldehyde by the reaction of methanol with synthesis gas using a system containing a cobalt entity, a ligand and an iodine compound. The reaction is non-selective, producing a mixture of many products, and exhibits a low selectivity to acetaldehyde and a relatively low conversion rate. Among the sources of halogen atom availability, lithium iodide is mentioned at column 4, line 24, but the patent does not disclose use of mixtures of rhodium and cobalt.

The reaction of methyl acetate with synthesis gas to produce acetic anhydride is shown in U.S. Pat. No. 4,251,458, issued Feb. 17, 1981 to J. Pugach using a Group VIII noble metal component with a halogen component and an arsenic component. Though alkali metal halides are mentioned, there is no data supporting production of acetaldehyde. Nor does the patent contain any recognition of the benefits to be achieved by any specific halogen composition or a mixture of rhodium and cobalt atoms.

In U.S. Pat. No. 4,267,384, acetaldehyde is produced by the reaction of formaldehyde with synthesis gas using a ruthenium-halide system. The rates and selectivities to acetaldehyde are poor and the reaction produces one mole of water for each mole of acetaldehyde, necessitating the removal of water. The patent does not disclose the production of aldehydes from organic esters using mixtures of rhodium and cobalt metal atoms plus lithium iodide.

In Japanese Publications Nos. 77/136110, and 77/136111, filed by Saito et al and published on Nov. 14, 1977, there are disclosed cobalt catalysts promoted with an iodine compound and employing a phosphorus compound to react methanol with synthesis gas to produce acetaldehyde. In neither publication is there any mention of lithium iodide or mixtures of rhodium and cobalt metal atoms and both show low selectivities.

Japanese Publication No. 77/133914, filed by Saito et al and published on Nov. 9, 1977, relates to the reaction of methanol with synthesis gas to produce acetaldehydes using a system containing cobalt, a halide promoter and at least one element of the group, arsenic, antimony and bismuth. There is no disclosure of advantages to be gained from any specific halogen component or mixtures of rhodium and cobalt metal atoms and selectivities were low.

U. K. patent application No. 2,001,070A, filed by A. Saus and published on Jan. 24, 1979, relates to the homologation of esters with synthesis gas to produce a higher homolog of the charged ester. The catalyst system contains at least one of the metals cobalt, rhodium, ruthenium or iron and an iodine promoter. There is no suggestion or disclosure of the unexpected results to be achieved using lithium iodide or mixtures of rhodium and cobalt metal atoms.

The preparation of acetaldehyde by the reaction of methyl acetate with synthesis gas is the subject of U.K.

patent application No. 2,038,829A filed by R. V. Porcelli and published on July 30, 1980. The catalyst system contains palladium, an iodine moiety (preferably methyl iodide), an organic promoter containing nitrogen, phosphorus, arsenic or antimony, and/or an inorganic promoter of elements having an atomic weight greater than 5 of Groups IA, IIA, IIIA, IVB, VIB and the non-noble metals of Group VIII. The reaction requires the use of the expensive palladium and excessive amounts of methyl iodide, a compound which is considered highly corrosive and thus very undesirable. It does not disclose the use of mixtues of rhodium and cobalt metal atoms.

U.K. patent application No. 2,067,557A, published July 30, 1981 and filed by Pugach, discloses the production of acetic anhydride by the carbonylation of methyl acetate or dimethyl ether using a Group VIII noble metal catalyst, a halide and multiple promoters which must include zirconium metal as one of the promoters in the presence of acetic acid under essentially anhydrous conditions. The halides are generically disclosed and there is no recognition of the use of lithium iodide with a cobalt-rhodium catalyst system, cobalt being a non-noble metal.

U.K. patent application No. 2,067,556A, published July 30, 1981 and filed by Pugach, discloses the production of acetic anhydride by the carbonylation of methyl acetate or dimethyl ether using a Group VIII noble metal catalyst, a halide and multiple promoters which must include hafnium metal as one of the promoters in the presence of acetic acid under essentially anhydrous conditions. The halides are generically disclosed and there is no recognition of the use of lithium iodide with a cobalt-rhodium catalyst system, cobalt being a non-noble metal.

European patent application No. 0,025,702, published Mar. 25, 1981 and filed by Isshiki et al., pertains to the conversion of methyl acetate or dimethyl ether to ethylidenediacetate using a system containing a nickel or cobalt compound and an iodine or bromine compound in conjunction with a promoter. Though LiI is disclosed as a suitable halide, it is not used in any of the examples, nor is there any suggestion or recognition of the unexpected results to be achieved by its use in conjunction with mixtures of rhodium and cobalt metal atoms in the production of acetaldehyde from methyl acetate.

European patent application No. 0,022,735, published Jan. 21, 1981 and filed by Gauthier-Lafaye et al, relates to a process for the preparation of acetaldehyde by the carbonylation of methanol using synthesis gas. The catalyst system contains cobalt and ruthenium in the presence of at least one ionic halide and at least one alkyl halide. It does not disclose the use of rhodium-cobalt metal atom mixtures.

European patent application No. 0,026,280, published Apr. 8, 1981 and filed by Kubbeler et al, relates to a process for the preparation of acetic anhydride from methyl acetate or dimethyl ether using a nobel metal catalyst, iodide, and a mixture of zirconium and heterocyclic aromatic compound as promoter. It nowhere suggests the use of a mixture of rhodium and cobalt with lithium iodide as the promoter.

European patent application No. 0,028,474, published May 13, 1981 and filed by Isshiki et al, relates to a multi-step process for producing vinyl acetate. In the first step, methanol is hydrocarbonylated to produce a mixture containing acetaldehyde. The catalyst employed contains the cobalt or ruthenium atoms. Nowhere in this reference is there any suggestion or disclosure of the use of a mixture containing both rhodium and cobalt atoms or of the unexpected and unpredictable selectivity achieved.

European patent application No. 0,028,515, published May 15, 1981 and filed by Isshiki et al, relates to the production of ethylidenediacetate by the reaction of dimethyl acetal, acetaldehyde and methyl acetate, or acetaldehyde and dimethyl ether with carbon monoxide using a Group VIII metal atom and a halide. The process does not disclose the production of aldehydes, rather it uses aldehydes as starting materials. Nor does it recognize the unexpected benefits achieved by the use of a mixture of rhodium plus cobalt with lithium iodide as the promoter.

European patent application No. 0,031,606, published July 8, 1981 and filed by Drent, relates to the production of carboxylic acid by the reaction of a carboxylic acid ester with synthesis gas using a system containing a ruthenium compound, a Group VIII metal compound and a Group II metal iodide and/or bromide. The process is not our claimed process nor does it suggest or disclose the unexpected results achieved by our process with our reactants and system.

European patent application No. 0,031,784, published July 8, 1981, and filed by Gauthier-Lafaye et al., discloses a process for the homologation of esters to the next higher homolog. The catalyst system contains cobalt, ruthenium and iodine moieties; a combination of ionic and covalent halide is charged. A trace amount of acetaldehyde is reportedly produced as a by-product. It does not disclose the use of mixtures of rhodium and cobalt metal atoms.

In German Offenlegungsschrift DE No. 2,941,232 A1, filed by Hans-Klaus et al., and published on Apr. 23, 1981, methyl acetate is reacted with synthesis gas using a system containing rhodium in combination with rhenium, manganese, or ruthenium, halogen compound, aliphatic carboxylic acid and a heterocyclic aromatic compound having a quarternary nitrogen atom. The principal product obtained was ethylidenediacetate; there is no indication that acetaldehyde could be made. Nor was there any disclosure on the use of a mixture of rhodium and cobalt metal atoms in conjunction with lithium iodide.

It can be seen that the prior art contains many disclosures dealing with the catalytic production of aldehydes via the reaction of esters, alcohols and ethers with synthesis gas. In the reaction of an alcohol the accepted net reaction is:

$$ROH + CO + H_2 \rightarrow RCHO + H_2O$$

One of the disadvantages in many of these references is the formation of water with the eventual need to remove it from the desired organic product. This removal is both complicated and costly. Other disadvantages often include the simultaneous occurrence of other reactions leading to the formation of by-products, such as, dimethyl acetal, methyl acetate, ethanol, etc. These reactions compete with the aldehyde production resulting in low aldehyde rate and selectivity.

Many processes employed for the production of acetaldehyde in the first stage and ethanol in the second reaction stage involve the reaction of formaldehyde with synthesis gas using a catalyst system containing a source of ruthenium and a source of halide present at least during the first stage. The alkali metal halides are often mentioned as suitable halide sources, but no distinction is made between any specific one of the alkali metal halides or between any other halogen compound. As with the use of methanol as the starting material, the use of formaldehyde also results in the formation of a mole of water, which must subsequently be removed. The formaldehyde-synthesis gas reaction can be shown as:

$$HCHO + CO + H_2 \rightarrow CH_3CHO + H_2O$$

SUMMARY OF THE INVENTION

A catalyst system and process for the production of an aldehyde at high efficiency, selectivity and conversion rate by the reaction of an ester with carbon monoxide and hydrogen (synthesis gas) has been found. The catalyst charged to the reactor contains a mixture of rhodium and cobalt atoms in conjunction with lithium iodide and optionally an organic ligand. The use of the mixture of rhodium and cobalt atoms and lithium iodide in this system within the ranges defined results in unexpectedly high efficiency, high conversion rate or activity and high selectivity not heretofore achieved in the production of aldehydes.

DESCRIPTION OF THE INVENTION

In the catalytic reactions of synthesis gas or carbon monoxide in processes to produce oxygenated organic compounds there are several criteria required of the catalyst. The catalyst must be as stable as possible, it should have a high activity or conversion rate, and it should have as high a selectivity for the desired product as possible.

Stability of the catalyst relates to how long the catalyst remains functional before either breaking down or losing its catalytic effect.

Activity or conversion rate relates to the amounts of reactants the catalyst converts to product per unit of time, generally expressed in g. mole per liter per hour (g mole/l/hr).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective, improvement is always desirable.

The present invention is based on the unexpected and unpredictable discovery that a rhodium plus cobalt-lithium iodide system is an unexpectedly superior catalytic system for the production of aldehydes from esters at unexpected high selectivities and high conversion rates. It was also found that a ligand, $ER_3'''$, can also be present as an optional component of the system. This unexpected improvement in both selectivity and conversion rate is achieved when the system's rhodium and cobalt atom components are maintained within a defined range and when lithium iodide is present as the source of the halogen component in the system. Optionally a solvent and/or diluent can also be present. The improved catalyst system of this invention can be portrayed as containing the components Rh-Co-LiI-ER$_3'''$, wherein Rh is the rhodium containing compound, Co is the cobalt containing compound and ER$_3'''$ is optionally present.

In the process of our invention esters are reacted with carbon monoxide and hydrogen using a particular system containing rhodium atoms, cobalt atoms and lithium iodide. This system produces commercially desirable aldehydes at unexpectedly high rates and selectivities, with a minimum of by-products and without formation of water. The reaction that occurs with a simple ester is theoretically:

$$RCOOR' + CO + H_2 \rightarrow RCOOH + R'CHO$$

After separation of the two products, the RCOOH can be esterified with an alcohol R'OH and after drying the ester produced, RCOOR', it is recycled to the reactor. Thus, our process is one that essentially consumes only the alcohol, R'OH, in the production of the aldehyde, R'CHO, and recycling of the acid after removal of the aldehyde by adding the appropriate alcohol to the acid.

For example, if the initial ester is methyl acetate then the products formed are acetaldehyde and acetic acid; water is not formed in our process. The acetaldehyde is removed and in a separate reaction the methyl acetate is regenerated by the esterification of the acetic acid with added methanol. The water produced in the esterification is removed and the methyl acetate is cycled to the reactor. Thus, pure acetaldehyde is produced with the net reaction being conversion of methanol into acetaldehyde. In this process the acid is not consumed and it is present only as a carrier or transferring agent. Further, in this process anhydrous conditions exist during the reaction, thus minimizing equipment corrosion, and product separation and purification procedures.

Alternatively, the desired ester feedstock can be generated in situ in the reactor. For example, if acetaldehyde is desired then a methyl ester can be generated by co-feeding methanol and a carboxylic acid to the reactor. In this case, however, the water formed remains in the reactor and essentially anhydrous conditions would not prevail thus possibly negating one of the advantages of this invention, namely conducting the reaction under essentially anhydrous conditions.

The ester RCOOR' consists of a carboxylic acid fragement RCO— and an alcohol fragment —OR'. As long as the —OR' fragment remains the same the same aldehyde is produced from any ester regardless of the carboxylic acid fragment. For instance, acetaldehyde would be produced from any methyl ester, e.g., methyl acetate, methyl propionate, methyl butyrate, etc., and the respective acid would be acetic acid, propionic acid, butyric acid, etc., thus affording flexibility in the carboxylic acid produced and in the esterification step since some acids may be easier to esterify than others. One can also use compounds having more than one ester linkage, for example, R'OOCR"COOR' esters, in which R" is a divalent hydrocarbyl group of the types defined for R and R' having from 2 to 10 carbon atoms.

In the above formulas R and R' can be the same or different monovalent hydrocarbyl groups and can be an alkyl group having from 1 to 30 carbon atoms, preferably from 1 to 15 carbon atoms and most preferably from 1 to 5 carbon atoms; an alkenyl group having from 2 to 30 carbon atoms, preferably from 2 to 15 carbon atoms and most preferably from 2 to 5 carbon atoms; or an aryl, aralkyl or alkaryl group having 6 or 10 ring carbon atoms, e.g., phenyl or naphthyl, which can be substituted with groups having from 1 to 10 carbon atoms, preferably 1 to 4 carbon atoms, in the alk-moiety thereof. The R and R' groups can be linear or branched and they can be unsubstituted or substituted with groups which will not have an adverse effect on the reaction; further; the alkenyl groups can contain more than one unsaturated bond. R can also be hydrogen.

Illustrative of suitable esters one can mention methyl formate, ethyl formate, isobutyl formate, methyl acetate, ethyl acetate, the propyl acetates, the butyl acetates, the decyl acetates, 2-ethylhexyl acetate, stearyl acetate, phenyl acetate, benzyl acetate, vinyl acetate, allyl acetate, methyl propionate, ethyl propionate, isopropylpropionate, methyl butyrate, ethyl butyrate, iso-propyl butyrate, methyl benzoate, propyl benzoate, methyl salicylate, iso-propylsalicytate, dimethyl malonate, diethyl malonate, dimethyl succinate, diisopropyl succinate, dimethyl maleate, dimethyl phthalate, diisobutyl phthalate, methyl cinnamate, iso-butyl cinnamate.

The rhodium component of the catalyst system can be supplied from any number of sources, many of these are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone rhodium. Among the materials which may be charged to the reaction zone to provide the rhodium component of the catalyst system of the present invention are rhodium metal, rhodium salts and oxides, organo rhodium compounds, coordination compounds of rhodium, and the like. Specific examples of materials capable of providing the rhodium constituent of the catalyst system of the present invention may be taken from the following non-limiting partial list of suitable materials.

$RhCl_2$
$RhBr_3$
$RhI_2$
$RhCl_3 3H_2O$
$RhBr_3 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$RhCl[(C_6H_5)_3P]_2(CH_3I)_2$
$Rh(SnCl_3)[(C_6H_5)_3P]_2$
$RhCl(CO)[C_6H_5)_3As]_2$
$RHI(CO)[(C_6H_5)_3Sb]_2$
$[(n-C_4H_9)_4N][Rh(CO)_2X_2]$ where X=Cl—, Br—, I—
$[(n-C_4H_9)_4AS]_2[Rh(CO)_2Y_4]$ where X=Br—, I—
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI[(C_6H_5)_3P]_3$
$RhCl[C_6H_5)_3P]_2$
$RhCl[(C_6H_5)_3P]_3H_2$
$[(C_6H_5)_3P]_3Rh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ The rhodium metal atom concentration can vary over a wide range. Enough metal atom must be present to achieve reasonable reaction rates; however, an excess may on occasion result in undesired by-products formation.

The cobalt component of the catalyst system can be supplied from any number of sources, many of these are known to those of ordinary skill in the art. Thus, it is not necessary for an understanding thereof to specifically enumerate every suitable type and every specific compound since any of the known compounds can be used. Nevertheless, descriptive of some of the useful cobalt sources are the known cobalt carboxylates such as cobalt formate, cobalt acetate, cobalt benzoate, cobalt toluate, cobalt propionate, cobalt butyrate, cobalt valerate, cobalt hexanoate, cobalt cyclohexylbutyrate, and the like; the cobalt carbonyls such as dicobalt octacarbonyl, acetyl cobalt tetracarbonyl, tricobalt dodecacarbonyl, and the like, including their phosphine substituted analogs many of which are known to those skilled in the art; the cobalt oxides such as cobalt oxide; cobalt hydroxide; cobalt halides such as cobalt iodide; cobalt carbonate; cobalt bicarbonate; cobalt. Any of the known cobalt complexes can also be used; for example, those of the type $Co(X)_n(ER_3''')_m$ in which X is a halogen atom and $ER_3'''$ is as hereinafter defined. Mixtures of cobalt compounds can be used. When a cobalt halide is used, proper adjustment is required to maintain the cobalt ratio as defined in this invention.

The cobalt concentration can vary over a wide range. Enough cobalt atom must be present in order to achieve reasonable reaction rates; however, excess cobalt can result in undesired by-products formation. The mole ratio of cobalt to ester can vary from 1:25 to 1:2000, the preferred range is from about 1:50 to 1:500, with the most preferred range being from about 1:100 to 1:400.

The mole ratio of rhodium to cobalt atom can vary in the limited range of about 10:1 to 1:10. It has been observed that best aldehyde conversion rates and selectivities are obtained when the preferred ratio of about 3:1 to 1:3, most preferably 1:1, is used. Enough rhodium and cobalt atom must be used to achieve reasonable reaction rates.

The mole ratio of rhodium to organic ester charged should be from about 1:25 to 1:2000, preferably from 1:50 to 1:500, with the most preferred range being from about 1:100 to 1:400.

The other component of the system is lithium iodide. It can be charged directly, or it can be formed in situ by any combination of lithium compound and iodine component that will result in the formation of lithium iodide during the reaction. Lithium bromide can also be used but the iodide is preferred. The presence of lithium iodide or lithium bromide is a critical feature of this invention. Direct charge of lithium iodide is the preferred form; however, a convenient combination for in situ formation of lithium iodide can be used. This includes the use of lithium carboxylates, carbonates and the like with a halogen compound. A suitable combination for in situ formation is lithium carboxylate and an alkyl halide. It is preferable to use a lithium carboxylate salt having the same organic moiety as the ester feedstock and methyl iodide when a methyl ester is used.

Sufficient lithium iodide or bromide must be present to exert a promoting effect on the reaction and to result in high conversion rates and selectivities to the corresponding aldehyde. The mole ratio of LiI:Co:Rh can vary over a wide range. A LiI:Co:Rh mole ratio of from 50:1:1 to 1:50:50 can be economically employed, the preferred range is from about 10:1:1 to 1:10:10 and most preferably is from about 4:1:1 to 1:4:4.

The mole ratio of Li:Co or Li:Rh can vary from 50:1 to 1:50, preferably from 10:1 to 1:10 and most preferably from 4:1 to 1:4.

As indicated, an organic ligand of the general formula $ER_3'''$ can optionally be present in the reaction system. The use of such ligands is known, as are their identities, to those skilled in this art. In this formula E represents a Group VA element, e.g., N, P, As, Sb and Bi, and $R'''$ represents an organic moiety. The ligand serves as a catalyst stabilizer and/or to further enhance efficiency, conversion rate and selectivity, especially when the reaction is carried out at higher temperatures, for example at about 200° C. or above. The ligand also serves to inhibit equipment corrosion in some instance. However, the use of a ligand is not mandatory and the reaction can be carried out without it.

A large number of organic ligands is known and any of these can be used provided they do not have an adverse effect on the reaction. Among those of particular utility are the tertiary amines and the tri- and pentavalent phosphorus compounds. Though those skilled in the art know these compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl(3-methoxyphenyl)phosphine, dibutyl stearylphosphine, tribenzylphosphine, dipropyl phenylphosphine, ethyl dipropylphosphine, tricyclohexylphosphine, cyclohexyl dibutylphosphine, propyl diphenylphosphine, dipropyl phenylphosphine, phenyl diethylphosphine, tridecylphosphine, trioctadecylphosphine, tribenzylphosphine, methyl diethylphosphine, ethyl diphenylphosphine, tolyl diethylphosphine, cyclohexyl diethylphosphine, diethyl cyclohexylphosphine, bis-(diphenylphosphino)ethane, bis-(diethylphosphino)-propane, bis-(diphenylphosphino)-butane, bis-(diethylphosphino)-octane, trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chlorophenyl)-amine, dibutyl phenylamine, dipentyl cyclopentylamine, ethyl diphenylamine, trinaphthylamine, tri-p-tolylamine, tri-benzylamine, tri(3-methylcyclohexyl)amine, and the arsines, stibines and bismuthines corresponding to the above-identified phosphines and amines. These and many others are known in the art. They can be used singly or, if one desires, mixtures containing two or more ligands can be used. One can also employ a phosphine oxide or phosphite corresponding to the above phosphines as the ligand; these are also well known.

The concentration of ligand charged can vary from a molar ratio of ligand to cobalt to rhodium of from about 50:1:1 to 1:50:50, preferably from 10:1:1 to 1:10:10, most preferably about 4:1:1 to 1:4:4. The reaction can be effectively carried out at $LiI:ER_3'''$; Rh:Co mole ratios of 4:4:1:1; though any ratio fitting the above description can be used.

In addition to the ligand one can optionally have a solvent present. Many solvents are known as useful, essentially inert, diluents and illustrative thereof one can mention 1,4-dioxane, the polyethylene glycol di-ethers or esters, diphenyl ether, sulfolane, toluene, carboxylic acids (especially the carboxylic acid used in the organic ester feedstock), as well as any other diluent or solvent which does not interfere with the reaction to any significant extent. The reaction is preferably carried out in the absence of any solvent or diluent other than those required to introduce reactants or catalyst components.

The reaction is carried out at a temperature of from about 100° C. to 300° C., preferably from 140° C. to 250° C. and most preferably from 150° C. to 225° C.

The pressure of the reaction can be from about 500 psig to 10,000 psig, preferably from 1,000 psig to 6,000 psig, most preferably from 1,000 psig to 3,000 psig. It has been observed that under similar conditions lower pressures can be used with the rhodium and cobalt atoms mixture employed as the catalyst in this invention than could be used to achieve the same results when only one of these metal atoms is used.

The mole ratio of $H_2:CO$ in the synthesis gas feed mixture can range from 1:10 to 10:1, preferably from 5:1 to 1:5 and most preferably from 2:1 to 1:2.

The reaction time varies depending upon the reaction parameters, reactor size and charge, and the individual components employed at the specific process conditions. The reaction can be a batch or continuous reaction.

The experiments and examples detailed below were carried out in a Hasteloy ® steel autoclave reactor having a volume of 300 ml, which was equipped with temperature and pressure sensing means, heating and cooling means, agitator and inlet and outlet means for introducing and removing components from the reactor. The autoclaves used in the synthesis gas reactions are well known in the art and can be used in this process.

Prior to charging the reactants the autoclave was washed with methanol at 100° C. under a synthesis gas pressure of 500 to 1,000 psig by agitating for 30 minutes. The autoclave was drained, rinsed with dry acetone, and dried with nitrogen or other inert gas. The liquid components were charged to the cleaned autoclave first and then the solid components were added and stirred. The autoclave was closed, purged with carbon monoxide or synthesis gas and then pressurized to 500 psig with carbon monoxide or synthesis gas. The autoclave contents were heated to the selected temperature, with agitation (usually 750 rpm), in about 45 minutes. As soon as the desired temperature was reached, the autoclave was brought to the desired reaction pressure plus 100 psig. The reaction was allowed to consume gas until the pressure had fallen to 100 psig below the desired pressure. The reactor was then repressurized to 100 psig above the desired pressure. One such cycle is considered 200 psig gas uptake. Unless otherwise specified the reactions were allowed to proceed until 3,000 psig gas uptake had occurred.

At the end of a reactor run, the contents were cooled, generally to about 10° C. A vapor phase sample was taken for gas chromatography analysis of gaseous components; the gas phase was vented through two dry-ice acetone traps and then through a 10 liter saturated solution of calcium hypochlorite to remove metal carbonyls. The reactor was pressurized three times with nitrogen, 90 psig, and vented through the same system.

The residual reactor contents were dumped into a chilled pressure bottle and sealed. Subsequent analysis was performed using a Hewlett-Packard Model 5880 gas chromatograph equipped with two columns one-eighth inch in diameter by ten feet long connected in series. The columns were packed with Chromosorb 101.

The following examples serve to further illustrate this invention. In all examples conversion rates and selectivities include acetaldehyde plus the acetaldehyde equivalents in dimethylacetal or paraldehyde.

EXAMPLE 1

The autoclave was charged with 1.25 g of cobalt acetate tetrahydrate (5 mmoles), 2.06 g of rhodium dicarbonyl acetylacetonate (8 mmoles), 4.28 g of lithium iodide (32 mmoles) and 150 ml of methyl acetate (1.9 moles). Following the procedure described above the reactor contents were heated to 180° C. and the pressure adjusted to 3,000 psig using a $H_2$:CO mixture having a 1:1 mole ratio. The reaction commenced upon pressuring to about 3,000 psig as evidenced by constant uptake of gas and was continued for 95 minutes at 3,000±100 psig for a total gas consumption of 3,000 psig. The reactor was then cooled and treated as described above. Analysis indicated the following products were produced:

Acetaldehyde—0.31 mole
Acetic acid—0.35 mole
Methane—Trace
Ethyl acetate—0.03 mole The remainder of the product mixture removed from the reactor was unreacted methyl acetate that had not been given adequate time to react. The rate to acetaldehyde was 1.34 gmoles/L/hr. The selectivity to acetaldehyde is about 86%, excluding acetic acid.

The example shows the excellent material balance and selectivity to acetaldehyde achieved. Theoretically one would expect the acetic acid:total acetaldehyde equivalents molar ratio to be 1:1; in this instance it is 0.9:1. The selectivity achieved is also exceptionally good. Further, absence of acetic anhydride and ethylidene diacetate was completely unexpected and unpredictable in view of the prior art teachings and considering the results achieved in Comparative Runs A and B shown in Table I. Based on the literature one would have expected ethylidene diacetate as the primary product.

EXAMPLE 2

A series of runs was carried out varying the rhodium-cabalt mole ratio. The reactants and procedure followed were as discussed in Example 1 except that the pressure was maintained at 2,000 psig±100 psig. The concentrations of rhodium atom and cobalt atom and the results achieved are summarized in Table I. Runs A and B are comparative runs containing either rhodium or cobalt only.

TABLE I

| Run | A* | B* | C | D | E | F |
|---|---|---|---|---|---|---|
| Catalyst Charge | | | | | | |
| Rh, mmole | 8 | 0 | 8 | 8 | 8 | 8 |
| Co, mmole | 0 | 8 | 2.5 | 5 | 8 | 10 |
| LiI, mmole | 32 | 32 | 32 | 32 | 32 | 32 |

TABLE I-continued

| Run | A* | B* | C | D | E | F |
|---|---|---|---|---|---|---|
| Rh:Co m ratio | — | — | 1:0.31 | 1:0.63 | 1:1 | 1:1.25 |
| Products Recovered (Liquid), wt. % | | | | | | |
| Acetaldehyde | 2.7 | 6.0 | 2.9 | 2.8 | 7.6 | 5.1 |
| Ethyl acetate | 1.8 | 0 | 1.4 | 2.3 | 3.1 | 4.0 |
| Ethylidene diacetate | 10.4 | 0 | 4.6 | 1.1 | 0 | 0 |
| Analytical Results | | | | | | |
| Methyl acetate conversion, % | 37 | 11 | 33 | 37 | 31 | 26 |
| Conversion rate** | 0.23 | 0.3 | 0.22 | 0.75 | 0.8 | 0.6 |

*Comparative runs
**To acetaldehyde, gmoles/L/hr

The data shows that as the Rh:Co mole ratio approaches 1:1, the amount of undesirable ethylidene diacetate decreases to zero. Also recovered were acetic acid and trace amounts of methane.

EXAMPLE 3

A series of runs was carried out to demonstrate the effect of addition of ligand, triphenylphosphine, to the reaction. The procedure followed and reactants charged were as described in Example 1. There were used 8 mmoles each of rhodium and cobalt atom and 32 mmoles of lithium iodide but the amount of triphenylphosphine was varied. The presence of triphenylphosphine enhanced the rate to acetaldehyde; further, in all instances there was no formation of ethylidene diacetate. The results are summarized in Table II; acetic acid and trace amounts of methane were observed in all runs.

TABLE II

| Run | A | B | C | D |
|---|---|---|---|---|
| Triphenylphosphine, mmoles | 0 | 8 | 24 | 32 |
| Products Recovered (Liquid), wt. % | | | | |
| Acetaldehyde | 7.6 | 8.6 | 8.2 | 7.7 |
| Ethyl acetate | 3.1 | 2.3 | 2.3 | 2.4 |
| Ethylidene diacetate | 0 | 0 | 0 | 0 |
| Analytical Results | | | | |
| Methyl acetate conversion, % | 31 | 30 | 34 | 33 |
| Conversion rate* | 0.8 | 1.1 | 1.1 | 0.95 |

*To acetaldehyde, gmoles/L/hr

EXAMPLE 4

A series of runs was carried out to demonstrate the effect of varying the lithium iodide concentration. The procedures followed and reactants charged were as described in Example 1; rhodium and cobalt atoms were charged. It was shown that the relationship of ratio of LiI:Rh:Co has an effect on selectivity at constant Rh:Co ratio. The results are summarized in Table III; acetic acid and trace amounts of methane were observed in all runs.

TABLE III

| Run | A | B | C | D |
|---|---|---|---|---|
| Lithium iodide, mmoles | 16 | 32 | 64 | 64 |
| Triphenylphosphine, mmoles | 0 | 8 | 8 | 24 |
| LiI:Rh:Co | 2:1:1 | 4:1:1 | 8:1:1 | 8:1:1 |
| Products Recovered (Liquid), wt % | | | | |
| Acetaldehyde | 3.0 | 8.6 | 3.8 | 2.8 |
| Ethyl acetate | 7.1 | 2.3 | 0.6 | 0.8 |
| Ethylidene diacetate | 0 | 0 | 14 | 9.2 |
| Analytical Results | | | | |

TABLE III-continued

| Run | A | B | C | D |
|---|---|---|---|---|
| Methyl acetate conversion, % | 29 | 30 | 50 | 57 |
| Conversion rate* | 0.3 | 1.1 | 0.5 | 0.3 |

*To acetaldehyde, gmoles/L/hr

EXAMPLE 5

A series of runs was carried out varying the pressure. The procedures followed and reactants charged were as described in Example 1. The catalyst was a mixture of 8 mmoles each of rhodium and cobalt atoms. The results are summarized in Table IV; acetic acid and trace amounts of methane were observed in all runs.

TABLE IV

| Run | A | B | C |
|---|---|---|---|
| Lithium iodide, mmoles | 32 | 32 | 32 |
| LiI:Rh:Co | 4:1:1 | 4:1:1 | 4:1:1 |
| Triphenylphosphine, mmoles | 24 | 32 | 0 |
| Triphenylamine, mmoles | 0 | 0 | 16 |
| Temperature, °C. | 180 | 180 | 200 |
| Pressure, psig | 2000 | 1500 | 1000 |
| Products Recovered (Liquid), wt % | | | |
| Acetaldehyde | 8.2 | 7.1 | 3.1 |
| Ethyl acetate | 2.3 | 2.7 | 1.5 |
| Ethylidene diacetate | 0 | 0 | 3.1 |
| Methane (gas) | | | |
| Analytical Results | | | |
| Methyl acetate conversion, % | 34 | 36 | 40 |
| Conversion rate* | 1.1 | 0.8 | 0.3 |

*To acetaldehyde, gmoles/L/hr.

We claim:

1. A process for the reaction of an organic ester having the structural formula RCOOR' or R'OOCR''COOR' in which R and R' are monovalent hydrocarbyl (i) alkyl groups having from 1 to 30 carbon atoms, (ii) alkenyl groups having from 2 to 30 carbon atoms, or (iii) aryl, aralkyl or alkaryl groups having from 6 to 10 ring carbon atoms and from 1 to 10 carbon atoms in the alk-moiety thereof, and R'' is a divalent hydrocarbyl group as defined for R and R' having from 2 to 10 carbon atoms, and wherein R can also be hydrogen, with carbon monoxide or synthesis gas to selectively produce an aldehyde, said process conducted at a temperature of from 100° C. to 300° C., a pressure of from 500 psig to 10,000 psig, wherein said synthesis gas has a $H_2:CO$ mole ratio of from 1:10 to 10:1, in contact with a mixed cobalt and rhodium homogenous catalyst system containing lithium iodide or lithium bromide as the promoter, wherein the mole ratios of Li:Co and Li:Rh are from 50:1 to 1:50, the Li:Co:Rh mole ratio is from 50:1:1 to 1:50:50 and the Rh:Co ratio is from 10:1 to 1:10.

2. A process as claimed in claim 1 wherein the temperature is from 150° C. to 225° C., the pressure is from 1,000 psig to 3,000 psig and the $H_2:CO$ mole ratio is from 2:1 to 1:2.

3. A process as claimed in claim 1 wherein the mole ratio of Li:Co and Li:Rh is from 10:1 to 1:10.

4. A process as claimed in claim 1 wherein the mole ratios of Li:Co and Li:Rh are from 4:1 to 1:4 and the mole ratio of Li:Co:Rh is from 4:1:1 to 1:4:4.

5. A process as claimed in claim 1 wherein said organic ester is methyl acetate.

6. A process as claimed in claim 4 wherein said organic ester is methyl acetate.

7. A process as claimed in claim 1 wherein an organic ligand of the formula $ER_3'''$ is present, wherein E is nitrogen, phosphorus, arsenic, antimony and bismuth and R''' is an organic moiety.

8. A process as claimed in claim 5 wherein an organic ligand of the formula $ER_3'''$ is present, wherein E is nitrogen, phosphorus, arsenic, antimony and bismuth and R''' is an organic moiety.

9. A process as claimed in claim 5 wherein an organic ligand of the formula $ER_3'''$ is present, wherein E is nitrogen, phosphorus, arsenic, antimony and bismuth and R''' is an organic moiety.

10. A process as claimed in claim 6 wherein an organic ligand of the formula $ER_3'''$ is present, wherein E is nitrogen, phosphorus, arsenic, antimony and bismuth and R''' is an organic moiety.

11. A process as claimed in claim 7 wherein said ligand is a tertiary amine.

12. A process as claimed in claim 8 wherein said ligand is a tertiary amine.

13. A process as claimed in claim 9 wherein said ligand is a tertiary amine.

14. A process as claimed in claim 10 wherein said ligand is a tertiary amine.

15. A process as claimed in claim 7 wherein said ligand is a phosphine.

16. A process as claimed in claim 8 wherein said ligand is a phosphine.

17. A process as claimed in claim 9 wherein said ligand is a phosphine.

18. A process as claimed in claim 10 wherein said ligand is a phosphine.

* * * * *